United States Patent [19]

Deugau et al.

[11] Patent Number: 5,508,169
[45] Date of Patent: Apr. 16, 1996

[54] INDEXING LINKERS

[75] Inventors: Kenneth V. Deugau, Kingston; Paul Unrau, Deep River, both of Canada

[73] Assignees: Queen's University at Kingston, Kingston; Atomic Energy of Canada Limited, Ottawa, both of Canada

[21] Appl. No.: 331,152

[22] Filed: Oct. 28, 1994

Related U.S. Application Data

[63] Continuation of Ser. No. 55,260, May 3, 1993, abandoned, which is a continuation of Ser. No. 505,884, Apr. 6, 1990, abandoned.

[51] Int. Cl.$^6$ .............................. C12Q 1/68; C12P 19/34; C07H 21/02; C12N 15/00
[52] U.S. Cl. .................... 435/6; 435/91.1; 435/91.2; 435/810; 536/23.1; 536/24.33; 536/25.3; 935/1; 935/8; 935/16; 935/76; 935/77; 935/78
[58] Field of Search .............................. 435/6, 91.1, 91.2, 435/810; 536/23.1, 24.33, 25.3; 935/1, 8, 16, 76, 77, 78

[56] References Cited

U.S. PATENT DOCUMENTS

| | | | |
|---|---|---|---|
| 4,719,179 | 1/1988 | Barany | 435/172.1 |
| 4,935,357 | 6/1990 | Saybalski | 435/91 |

OTHER PUBLICATIONS

New England BioLabs® 1988–1989 Catalog, p. 63.
Mormeneo et al., "Precise Nucleotide Sequence Modifications with Bidirectionally cleaving Class IIS excision Linkers", *Gene*, vol. 61, No. 1, 1987, pp. 21–30; Abstract Only.
Sommer and Tautz, *Nucleic Acids Research*, vol. 17, No. 16, 1989, p. 6749.

*Primary Examiner*—W. Gary Jones
*Assistant Examiner*—Bradley L. Sisson
*Attorney, Agent, or Firm*—Oblon, Spivak, McClelland, Maier & Neustadt

[57] ABSTRACT

Synthetic nucleic acid molecules are provided which are called indexing linkers and which can be selectively linked to unknown, or non-identical cohesive ends of nucleic acid fragments. Such indexing linkers are useful for the selective isolation, identification, amplification, labelling, and modification, of nucleic acid fragments, especially subsets of such fragments released by cleavage using Type IIS restriction endonucleases or restriction endonucleases recognizing interrupted palindromic sequences. Sets of such indexing linker molecules are described which are useful for indexing fragments released by cleavage of a genome. Methods are described for distinguishing such fragments using said indexing linker molecules for effecting detection, or further modification of such fragments; and for amplifying such fragments by the polymerase chain reaction.

33 Claims, 10 Drawing Sheets

INDEXING LINKERS

This application is a Continuation of application Ser. No. 08/055,260, filed on May 3, 1993, now abandoned, which is a continuation of application Ser. No. 07/505,884, filed on Apr. 6, 1990, now abandoned.

FIELD OF INVENTION

This invention relates to methods for identifying nucleic acid molecules and to indexing linker molecules and sets thereof which are useful in said identification and manipulation.

BACKGROUND OF THE INVENTION

The analysis of large nucleic acid molecules, whether entire genomes or single restriction fragments, usually involves characterization by size, location relative to other fragments of nucleic acid, identification of restriction endonuclease cleavage sites, and nucleotide sequence. These analyses typically require a recursive process of division or cleavage into smaller fragments, separation of these into smaller subsets or individual pieces, and finally the identification of the fragment of interest, typically by hybridization with a specific nucleic acid probe or by direct determination of the nucleotide sequence of the fragment. In practice, the analysis frequently begins with the preparation of a library of cloned nucleic acid fragments constituting an entire genome, or a particular subset of fragments, selected by some convenient criteria.

This identification process is time consuming and expensive because the available means of characterization and selection of nucleic acid fragments are too general (for example by restriction fragment length or by the presence of poly-A in mRNA) or too specific (for example the detection of unique sequences and sequences poorly represented in cloned libraries), or may require prior knowledge of some of the nucleic acid sequence (for example flanking sequences must be known in order to specify the nucleic acid primers needed for amplification of the intervening "target" sequence by the Polymerase Chain Reaction).

It would be useful to have some additional means of characterizing or "indexing" nucleic acid fragments which would permit manipulation and identification to be carried out more efficiently and at lower cost. Such a development would make a significant contribution to a wide variety of molecular biology projects, including such major tasks as the sequencing of the human genome.

Three important techniques have been developed for nucleic acid manipulation and analysis.

The first of these is molecular cloning. (See for example S. N. Cohen et al. (1973) Proc. Nat'l. Acad. Sci. U.S.A. 70:3240–3244, "Construction of Biologically Functional Bacterial Plasmids in vitro"). In its simplest form, this involves first cutting or breaking the target nucleic acid, i.e. DNA, into smaller fragments (typically by restriction endonuclease digestion) and inserting the fragments into a biological vector. The assortment of DNA fragments is then maintained and amplified by the replication of the vector DNA in vivo. Separation of the copies of cloned DNA in this "library" is accomplished by dilution and subsequent growth of bacterial colonies or phage plaques from single organisms bearing copies of only one of the original DNA fragments. Identification of the clones of interest is done by hybridization of a specific labelled probe with the DNA released from each colony or plaque.

More recently, a second technique was developed called the Polymerase Chain Reaction or PCR. (See for example Canadian Patent No. 1,237,685 of K. B. Mullis for "Process for Amplifying Nucleic Acid Sequences"). This technique can be used to isolate and amplify sequences of interest. The technique allows the definition of any "target" portion of a nucleic acid sequence by the sequences which lie adjacent to it. Consequently, hybridization of nucleic acid primers at these adjacent sites permits the replication of only the intervening target sequence and the adjacent primer sites. The selective amplification by repeated replication in this way results directly in the separation of the desired fragment (or subset of sequences) by effective dilution of all other unwanted sequences by replicated copies of the target sequence. Identification is then carried out by hybridization against a known probe, or more frequently, by simple size analysis by agarose or polyacrylamide gel electrophoresis to confirm that the desired target sequence has been amplified.

A third major technique used for comparative genomic analysis is called Restriction Fragment Length Polymorphism, or RFLP, analysis. See for example: D. N. Cooper and J. Schmidtke (1984) Human Genetics 66:1–16, "DNA Restriction Fragment Length Polymorphisms and Heterozygosity in the Human Genome". Insertions, deletions, and some types of single base substitutions can be detected and their inheritance (and the inheritance of other mutations known to be closely linked) determined. Specific individuals can uniquely identified from a modification of this technique known popularly as "DNA Fingerprinting". See for example: A. J. Jeffries et al. (1985) Nature 314:67–73, "Hypervariable 'Minisatellite' Regions in Human DNA". This third technique also begins with restriction endonuclease cleavage of genomic, cloned or PCR-amplified DNA, into fragments. The resulting fragments are separated according to size by gel electrophoresis, and certain target fragments or groups of fragments are identified by hybridization with a specific probe. In this case, the sizes of fragments identified by hybridization with the probe provide a measure of whether the target sequence complementary to the probe is part of an identical or analogous fragment from other individuals.

While each of these three techniques, and the many specific variations which have evolved from them, are extremely valuable in investigating various aspects of structure and organization of particular genes, they each suffer from disadvantages.

Molecular cloning of a mixture of all the fragments from a restriction endonuclease digest of genomic DNA may provide a library, which on statistical grounds, should contain representatives of all fragments. In fact there may be a selective bias against some sequences due to the spacing of the restriction sites, or the propensity of some sequences to mutate, rearrange or fail to replicate in vivo. See for example: U. Gubler and B. J. Hoffman (1983) Gene 25:263–269, "A Simple and Very Efficient Method for Generating cDNA Libraries", and T. Maniatis et al (1978) Cell 15:687–701, "The Isolation of Structural Genes from Libraries of Eukaryotic DNA", and K. Kaiser and N. Murray (1985) DNA Cloning, Vol. 1: A Practical Approach, "The Use of Phage Lambda Replacement Vectors in the Construction of Representative Genomic DNA Libraries". As a consequence, any sequence which is present in the library at low frequency may be very difficult to detect, requiring screening of large numbers of colonies or plaques. Another disadvantage is that subsequent manipulation to ensure the purity and identity of clones or to isolate smaller fragments of the target clone also contributes to significant delay and expense. That is, it is necessary either to undertake the expense of screening large numbers of clones to detect a low probability event directly, or to undertake the extra procedures of attempting to enrich the population of clones screened for the target of interest.

The major disadvantage of the PCR technique is the requirement for prior knowledge of the nucleic acid sequences flanking the region of interest which permits specification of the primers required to amplify that intervening sequence. Where applicable, this technique offers extremely high precision at relatively low cost, but is limited to targets which have already been the subject of investigation at least to the extent of obtaining the necessary flanking sequence information. A second disadvantage is that for non-repetitive analyses of large numbers of different targets, the cost of two unique primers required per target may become prohibitive. This technique is currently limited to a maximum distance between primer sites of only a few kilobases of DNA. This appears to be a minor limitation, but reduces the possibilities for investigation of larger structural and functional units in a genome.

In contrast to the PCR technique, RFLP analysis does permit comparisons to be made among fragments of unknown sequences. However it is limited to detections of certain types of mutations or variations, namely to significant insertions and deletions large enough to change the sizes of fragments, or to insertions, deletions or base changes within restriction endonuclease recognition sequences which prevent cleavage between two fragments or which generate new recognition sequences. In the absence of such polymorphic or polyallelic genetic markers closely linked to the loci of interest for genetic diagnosis, RFLP analysis is unable to provide the desired inferences about the inheritance or identity of these loci; see: D. N. Cooper and J. Schmidtke [supra]. The search for suitable probes and the characterization of such variant sites is thus a relatively inefficient trial and error process.

Each of these three important techniques for nucleic acid analysis has been outstandingly successful in those areas for which it is applicable. Each in turn has limitations based upon the limited information available about the fragments or groups of fragments, or conversely, based upon the limited ability to reduce the complexity of a mixture (i.e. to select and isolate a suitable subset) to permit more detailed investigation. It would be a powerful extension of all of these techniques to provide a method for subsetting complex mixtures of nucleic acids in a consistent and efficient manner, to provide a level of information intermediate between the relatively crude measure of sizes of restriction fragments, and the precision of partial or complete sequence determination. Three aspects of recombinant DNA technology are important in achieving such a method.

First, certain types of restriction endonucleases cleave DNA to reveal cohesive ends which may be non-identical and unrelated to the recognition sequence of the enzyme used. One group is called Type IIS or "shift" restriction endonucleases. See for example: W. Szybalski (1985) Gene 40:169–173, "Universal Restriction Endonucleases: Designing Novel Cleavage Specificities by Combining Adapter Oligodeoxyribonucleotide and Enzyme Moieties"; Kessler et al (1985) Gene 33:1–102, "Recognition Sequences of Restriction Endonucleases and Methylases—A Review". These Type IIS endonucleases cut DNA at sites removed by one or more bases from the recognition sequence (which is usually non-palindromic). A second group of restriction endonucleases have interrupted palindromic recognition sequences and they cut irrespective of the nature of the intervening sequences, provided that the intervening sequence is of the appropriate length.

The cohesive ends of the resulting DNA fragments may contain all possible permutations and combinations of nucleotides. For example the restriction endonuclease FokI (see Kessler et al [supra]) generates 4 base, 5'-cohesive ends, by cutting one strand 9 nucleotides 3'- to the recognition sequence GGATG and correspondingly on the opposite strand 13 nucleotides 5'- to the complementary CATCC sequence:

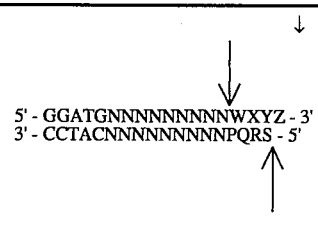

If a large genome was cut with this enzyme, then all $4_4$ or 256 possible tetranucleotide ends should be represented in the resulting mixture of DNA fragments.

A universal restriction endonuclease is described in published European patent application No. 234,781 (Szybalski). The universal endonuclease utilizes a tailored oligodeoxynucleotide adaptor in conjunction with a Class IIS endonuclease. The adaptor consists of a single stranded region complementary to a single stranded region of target DNA at the desired cleavage site. Adjacent to the single stranded region of the adaptor is a hairpin region containing the recognition sequence of the endonuclease. The adaptor is constructed so that the endonuclease will bind to a recognition sequence in the double stranded portion and will cleave the single stranded target region at the desired site, once the adaptor has been hybridized to the complementary region of the target DNA. The described adaptor is intended to be bound to target DNA only by means of base pairing. Consequently, the single stranded region of the adaptor, complementary to the target DNA, must be of sufficient length to anchor the adaptor throughout the cleavage process. The adaptor disclosed has a recognition sequence for FokI and a single stranded region of 14 nucleotides in which cleavage will occur. This teaching provides highly specific cleavage of single stranded DNA at any desired sequence.

Brenner, S. and Livak, K. J. (1989) Proc. Natl. Acad. Sciences USA 86:8902–8906 provide a method for characterizing DNA fragments by both size and terminal sequence. In their method, fragments are produced as a result of cleavage by a Type IIS endonuclease. In case of the endonuclease FokI, 4 base, 5'-single stranded overhangs having non-identical sequences were generated. DNA polymerase was used to attach fluorescent labelled nucleotides complementary to the bases in the 5'-cohesive ends. Cleavage using a different endonuclease was carried out resulting in the presence of some fragments having fluorescent labelled ends. Analysis of the fluorescently labelled DNA by gel electrophoresis in an automated DNA sequencing apparatus provided the sequence of the fragment cohesive ends produced by the Type IIS endonuclease cleavage and the length of the fragments.

The second aspect is similar to a prior invention: DNA adaptors. See for example: R. J. Wu et al, U.S. Pat. No. 4,321,365, "Oligonucleotides useful as Adaptors in DNA Cloning, Adapted Molecules, and Methods of Preparing Adaptors and Adapted Molecules". Adaptors are short double stranded DNA molecules with either one or both ends having protruding single stranded regions which are recognition sites of restriction endonucleases. They can be covalently attached to other DNA fragments bearing the complementary base pairs for the same restriction endonuclease recognition sequence (e.g. fragments generated as a result of cleavage of a larger fragment with the same endonuclease) using a polynucleotide ligase. This provides a tool for molecular cloning as the same adaptor molecule may be used to introduce any double stranded DNA into cloning vehicles at specific sites.

Finally, the third aspect is the ability to synthesize chemically any desired nucleic acid sequence by the phosphotriester method (see S. A. Narang et al. (1979) Methods Enzymol. 68:90–98 "Improved Phosphotriester Method for Synthesis of Gene Fragments) or the phosphoramidite method (for example see: M. D. Matteucci and M. H. Carruthers (1981) J.Amer. Chem. Soc. 103:3186–3191 "Synthesis of Deoxyoligonucleotides on a Polymer Support") offers the practical means to design and prepare oligonucleotide primers, probes, adaptors and linkers at will to suit any desired application.

OBJECTS OF THE INVENTION

It is an object of the invention to provide synthetic nucleic acid molecules called indexing linkers which can be selectively linked to (i.e. which will index) unknown, or non-identical cohesive ends of nucleic acid fragments such as those released by cleavage using Type IIS restriction endonucleases or restriction endonucleases recognizing interrupted palindromic sequences.

It is another object of the invention to provide sets of indexing linkers, each member of a set being able to index a particular cohesive end selected from the group of possible cohesive ends produced by endonucleases such as those described above. Such a set of linkers is useful for the indexing of any sub-set of a mixture of fragments of unknown or non-identical cohesive ends.

It is another object of the invention to provide methods for indexing nucleic acid fragments to facilitate comprehensive and reproducible categorization of the fragments, and rapid screening, direct detection, and isolation of the indexed fragments for subsequent manipulation and analysis.

It is yet another object of the invention to provide methods for selective amplification, analysis and manipulation of nucleic acid fragments using the above mentioned indexing linker molecules.

SUMMARY OF THE INVENTION

The inventors have appreciated that subsets of nucleic acid fragments may be indexed (i.e. selected or targeted) based upon the information contained in non-identical 5'-protruding or 3'-protruding cohesive ends, particularly those having 3,4 or 5 base cohesive ends, such as those revealed by cleavage of DNA by Type IIS restriction endonucleases and interrupted palindrome recognizing type II restriction endonucleases. The inventors have appreciated that, by using nucleic acid molecules similar to adaptors (herein called indexing linkers), containing protruding single strands complementary to the cohesive ends of cleavage sites of restriction endonucleases (rather than the recognition sequences), various functional groups or specific nucleic acid sequences designed for particular applications may be selectively attached to the aforementioned subsets of fragments.

The inventors have developed methods dependent on the use of one or more indexing linkers and procedures known in the prior art which permit selective isolation of nucleic acid fragments containing only one of all such cohesive ends, identification of the exact sequence of bases present in the cohesive ends of each subset of such fragments present alone or in a mixture, selective amplification by the polymerase chain reaction of fragments containing only one or two of all such possible cohesive ends without knowledge of the base sequence of their double stranded portions, selective labelling of one strand, or one end, of one or more subsets of fragments with indexing linker(s) containing detectable reporter groups, selective modification of one end, or one strand, of one or more subsets of fragments containing such cohesive ends to enable or disable the action of various enzymes which can act on nucleic acids such as polymerases, polynucleotide kinases, polynucleotide ligases, exonucleases, or restriction endonucleases, and rapid determination of restriction endonuclease maps of fragments cleaved with restriction endonucleases which reveal such cohesive ends.

Selective attachment of indexing linkers having known base sequences in their cohesive ends to a subset of fragments bearing the complementary cohesive ends can be used for the detection, identification, isolation, amplification, and manipulation of the subset of fragments. No prior knowledge of the identity (sequence) of the cohesive ends nor any knowledge of the internal sequences in the subset is required for such manipulation or characterization. The former can be inferred from the known cohesive ends of the indexing linkers used, and determination of the latter by hybridization or sequence analysis can be readily facilitated. These procedures are compatible with existing methodology, thus simplifying their introduction and extending the range of their potential applications.

This invention provides novel indexing linker molecules which having as an essential element a double stranded oligonucleotide with a first end having a protruding single strand of 3, 4, or 5 nucleotides, and a second end having a protruding single strand of any number of nucleotides including zero, characterized in that neither end, when paired with a complementary nucleotide cohesive end, will function as a restriction endonuclease recognition site.

This invention further provides a set of indexing linker molecules each of which having as an essential element an oligonucleotide with a first end having a protruding single strand of 3 or more nucleotides, and a second end having a protruding single strand containing any number of nucleotides including zero wherein the sequences of the protruding single strands of the first end of members of the set are different.

The invention further provides a method of modifying a nucleic acid fragment having at least one cohesive end, so as to distinguish said fragment, comprising: selecting one or more indexing linker molecules from the aforementioned set of indexing linker molecules, which selected molecule has a protruding strand of the first end which is exactly complementary to a fragment cohesive end; and attaching said indexing linker molecule to the fragment.

The invention further provides methods of effecting detection or further modification of a fragment by employing indexing linkers to impart an identifying feature, an enzyme specific or blocking site, or a restriction endonuclease sequence to a fragment.

The invention further provides a method of amplifying a nucleic acid fragment by a polymerase chain reaction, wherein a complementary indexing linker molecule is ligated to both 3'- and 5'-ends of the same strand to provide templates for hybridization of primer oligonucleotides.

BRIEF DESCRIPTION OF DRAWINGS

FIG. 6 Photograph of electrophoresis gel described in example 1.

FIG. 7 Photograph of electrophoresis gel described in example 2.

DETAILED DESCRIPTION OF THE INVENTION

Figure 1:
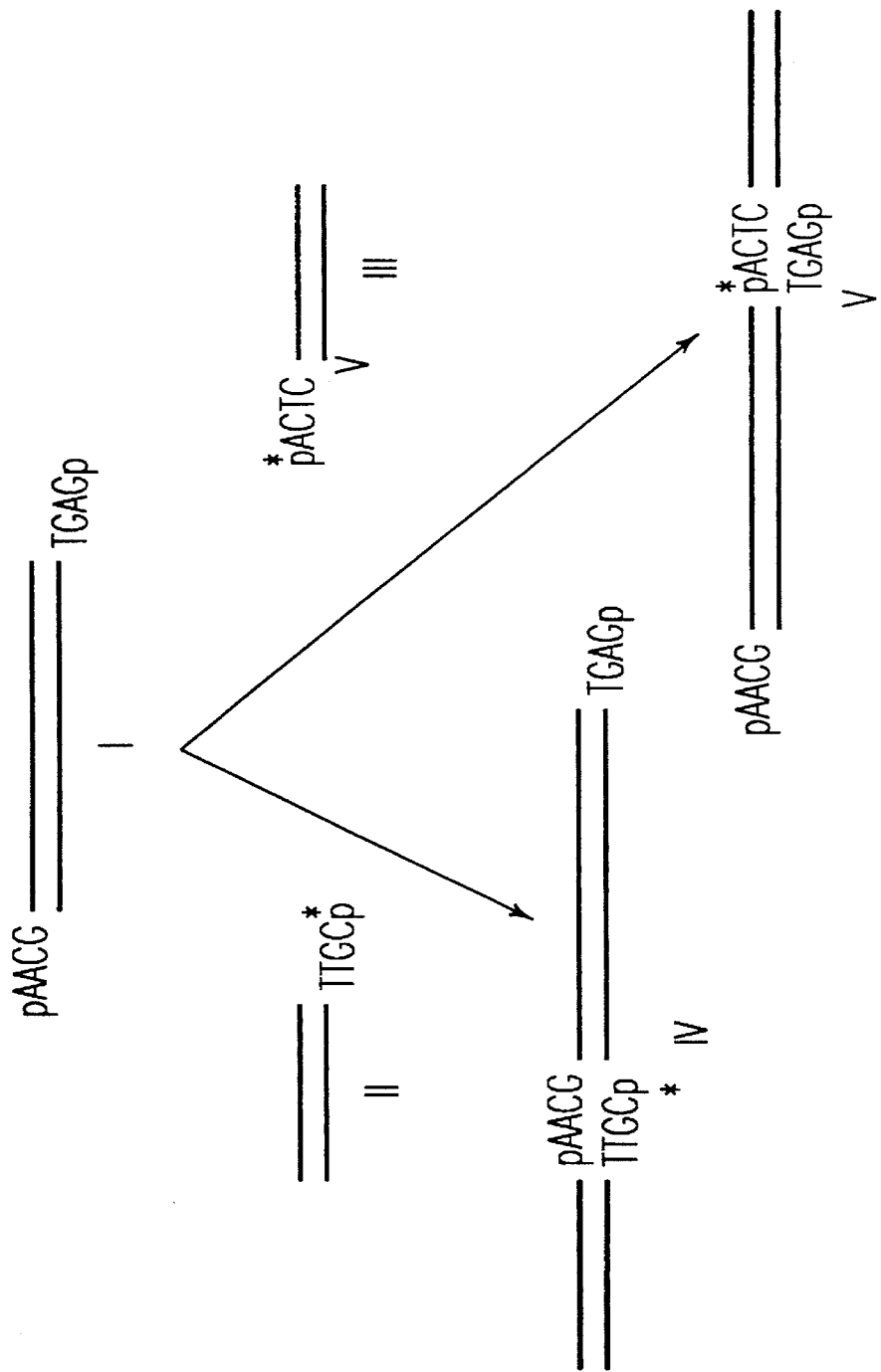
FIG. 1 Schematic diagram showing an example of a method of end identification and labelling.

This invention may be used to index nucleic acid fragments, preferably those containing 3, 4 and 5 base cohesive ends. The indexing linkers can be used in conjunction with Type IIS restriction endonucleases, that is enzymes which cleave DNA at locations outside of the recognition site and which generate cohesive ends. Examples of Type IIS restriction endonucleases are FokI, BbvI, HgaI, BspMI and SfaNI.

The indexing linkers can also be used in conjunction with restriction endonucleases which recognize interrupted palindrome sequences and cut the DNA irrespective of the intervening sequences to produce cohesive ends. Examples of interrupted palindrome recognizing restriction endonucleases are SfiI, BglI, and BstXI.

Both types of restriction endonucleases produce cohesive ends comprising permutations and combinations of the four nucleotides, A, C, G, and T. The larger the number of protruding bases, the greater the number of possible permutations and combinations of terminal nucleotide sequences, and the more specific the indexing is likely to be. A restriction endonuclease, such as SfiI, which releases fragments with three base, 3'-protruding cohesive ends will generate fragments having $4_3$ or 64 possible protruding trinucleotide ends and, since each fragment has two ends, $64^2$ or 4096 possible classes of fragments, each class or subset being defined by the identity of its two protruding trinucleotide ends. Since the orientation of the fragments cannot be known, the number of identifiable classes is actually $N \times (N+1)/2$ (where N is the number of possible ends). Therefore, in the above-mentioned case, the number of classes is 2080.

Cleavage of human genomic DNA (which has a haploid number of $3 \times 10^9$ base pairs) with the restriction endonuclease FokI will release a large and complex mixture of fragments with four base, 5'-protruding ends. On average, FokI cuts twice in every $4^5$ base pairs giving an average fragment size of 512 base pairs, and resulting in $3 \times 10^9 / 512 =$ approximately $6 \times 10^6$ fragments. There are $4_4 = 256$ possible tetranucleotide sequences and therefore 256 possible identities for each cohesive end. Thus there will be $256 \times 257/2 = 32,896$ possible classes of fragments, each class defined by the identity of its two ends. Each of these identifiable classes will contain on average $6 \times 10^6 / 32,896$, or about 200 fragments. It is reasonable to assume that the fragments in a class will vary in size. Therefore the fragments may be resolved, in most cases uniquely, by gel electrophoresis or some other high resolution technique.

It will be apparent that the number of different fragments in each identifiable class can vary from zero upwards. The number will depend upon at least two factors. Firstly, it will depend upon the number of protruding bases which occur on the cohesive ends produced by the action of the restriction endonuclease on the DNA. Secondly, it will depend upon the number of restriction sites for that restriction endonuclease in the DNA to be cleaved. Generally speaking, the smaller the number of restriction sites, and the larger the number of bases in the cohesive ends, the more specific will be the classification of fragments.

The use of a comprehensive panel of indexing linkers provides a means for attaching specific functional modifications to selected subsets of a complex mixture of nucleic acid fragments, preferably DNA, and identifying the molecules so modified. Such a defined subset of molecules may be further resolved by additional cleavage and indexing, or by any of the established techniques such as cloning, PCR amplification, gel electrophoresis, etc. Individual members of the class may be distinguished by identifying characteristics such as length, sequence, restriction endonuclease maps, etc. The sequence of the cohesive ends of the linkers provides a means of indexing a large number of subsets of double ended nucleic acid fragments (e.g. 2080 unique subsets of pairs of trinucleotide ends; 32,896 of tetranucleotide ends; and 524,800 of pentanucleotide ends).

This indexing and identification concept is adaptable to a variety of specific contexts in the dissection and analysis of nucleic acids from any source. It may also be adapted to use with single stranded DNA such as that cloned in single stranded vectors like M13 (see for example: W. Szybalski [supra]).

The indexing linker oligonucleotides of this invention may be prepared by methods known in the art. A preferable method is to synthesize the oligonucleotides by the phosphoramidite procedure on an automated synthesizer (such as the Biosearch 8750™) followed by purification by thin layer chromatography. Such a procedure is described in T. K. Archer et al (1985) J. Biol. Chem. 260:1676–1681 "Apolipoprotein C-II mRNA levels in Primate Liver". Preferably, the indexing linker molecule includes a double stranded oligonucleotide having a first end which is a protruding single strand of three or more nucleotides. The protruding single strand of the first end is the portion of the indexing linker molecule which will be complementary with the "target" cohesive end of a oligonucleotide fragment to be indexed. In one preferred embodiment, the oligonucleotide of the indexing linker molecule is DNA.

The indexing linker molecules may have a second end which is a protruding single strand oligonucleotide containing any number of nucleotides, to act as a desirable structural element (e.g. a protruding 3'-end to prevent exonuclease III cleavage). Preferably, the second end strand is of a different length than the first end strand so as to not interfere with the specificity of the linker for its target fragment.

It is preferable that the protruding single strand of the first end have three, four, or five nucleotides. A double stranded oligonucleotide portion of the indexing linker may have any convenient sequence or length. In a preferred embodiment, the double stranded portion of the indexing linker molecule is constructed so as to have within its sequence, the recognition sequence of a restriction endonuclease. Preferred recognition sequences are selected from the group consisting of the Type IIS restriction endonucleases including FokI, BbvI, HgaI, and SfaNI, and one half of a recognition sequence of an interrupted palindrome recognizing restriction endonuclease such as SfiI, BglI, and BstXI.

A set of indexing linker molecules according to this invention will include different indexing linker molecules having protruding single strands of the first end which comprise different sequences of nucleotides selected from possible combinations and permutations of the nucleotides A, C, G, and T. While the protruding first end single strands of indexing molecules in one set have different sequences, it is preferable that they be of the same length to facilitate use of the set to index fragments produced by cleavage by one endonuclease. It is preferable that the members of a set contain a double stranded portion which is identical for each member of the set.

A preferred embodiment of this invention is a set of indexing linker strands comprising: (a) at least two single stranded first oligonucleotides each having a common identical sequence, and a unique sequence of a length selected from 3, 4 and 5 nucleotides selected from permutations and combinations of A, G, C & T nucleotides, at one end selected from a 3' end and a 5' end; and (b) a single stranded second oligonucleotide whose sequence is complementary to said common sequence such that, when hybridized with any one of the first oligonucleotides, a double stranded indexing linker molecule would result which includes a first end having a protruding single strand comprising said unique sequence and a second end having a protruding single strand of any number of nucleotides including zero.

Methods are described herein which permit indexing of nucleic acid fragments by the attachment of indexing linkers to any class of the fragments having cohesive ends complementary to the protruding ends of the linker molecules, and which subsequently enable the selective detection, isolation, amplification, and mapping of that class of fragments. Examples of some of these methods are presented herein which demonstrate the elements of specificity and convenience of the indexing process. Other methods may be inferred readily from the examples and a knowledge of the prior art.

A primary instance of use of the indexing linkers is to identify specific cohesive ends of one or more DNA fragments obtained from restriction digests which yield non-identical cohesive ends. Identification may be effected by incorporation (by known methods) of detectable reporter groups such as a fluorescent tag (see for example: L. M. Smith et al. (1985) Nucl. Acids Res. 13:2399–2412), or a radioisoptope label (for example as described in: T. Maniatis, E. F. Fritsch and J. Sambrook, *Molecular Clonina: A Laboratory Manual*, Cold Spring Harbor Laboratory, 1982, pages 117 to 124), or an affinity ligand (such as a biotinyl moiety as described by: A. Chollet and E. H. Kawashima (1985) Nucl. Acids Res. 13:1529–1541), into the linker molecules. This permits the selective attachment of the aforementioned reporter groups, by means of the linkers, to DNA fragments The reporter groups will be covalently attached to the fragment if the linker is ligated to the fragment and the fragment may be identified by observing the presence of the reporter group.

When an affinity ligand such as the aforementioned biotinyl moiety is attached to the linker, fragments distinguished by attachment to such linkers may be separated from other fragments by attaching the aforementioned linkers to an appropriate affinity ligand binding moiety, by means known in the art. Thus, the distinguished fragments may be separated by known procedures of affinity chromatography.

A DNA fragment obtained from a cleavage by a Type IIS or interrupted palindrome recognizing enzyme may have any of the possible permutations and combinations of nucleotides in the resulting cohesive ends. In FIG. 1, this is indicated by the 5'-protruding sequences 5'-pAACG and 5'-pGAGT. Two indexing linkers (II,III) each having a protruding single stranded end complementary to one of the cohesive ends of the DNA fragment (I), and a detectable reporter group (*, which in this figure indicates a 5'-$^{32}$P group) are shown. Ligation of each linker to the DNA fragment results in the selective attachment of the linker to the corresponding complementary cohesive ends only. In the resulting product DNA molecules (IV and V respectively) the reporter group is seen to be attached selectively to one end and one strand only. These asymmetrically labelled DNA molecules are suitable for sequence analysis or hybridization, or DNA "footprinting". None of the other 254 possible 5'-protruding tetranucleotide linkers can be efficiently ligated to I. Thus, the identity of the cohesive ends of I can be inferred from the identities of the cohesive ends of the linkers which can be ligated.

Determination of the identity of cohesive ends present in each fragment of a restriction digest of a larger fragment, according to the known sequence of a complementary linker, permits a restriction map to be defined rapidly. This is because each cohesive fragment end must connect with the corresponding complementary cohesive end of the adjacent fragment. Preliminary mapping by this method would lead to rapid assignments of positions for other restriction endonuclease cleavages.

Isolation of subsets or classes of nucleic acid fragments having a specific cohesive end can be accomplished by using one or more indexing linkers attached to a insoluble support. Preferably, a panel of indexing linkers is attached to spatially segregated solid phase substrates which can be prepared by known procedures such as that as described by S. S. Ghosh and G. F. Musso (1987) Nucl. Acids Res. 15:5353–5372).

The target fragment with a complementary cohesive end may be ligated to the immobilized linker by known procedures such as that described by Z. Hostomsky et al. (1987) Nucl. Acids Res. 15:4849–4856. Ligation of fragments with a particular cohesive end occurs selectively to the immobilized indexing linker having the corresponding complementary cohesive end. Removal of the non-ligated fragments requires only a simple washing procedure. Subsequent recovery of the bound subset of fragments follows cleavage from the immobilized indexing linkers with a Type IIS restriction endonuclease or such other restriction endonuclease as the linkers may be designed to accommodate.

In an alternate method, one strand of the bound fragment may be eluted from the support by denaturation following a change in conditions (i.e. a rise in temperature). This would permit isolation of one strand of a particular linker— fragment complex. Thus, single strands may be isolated to serve as sequencing templates or for preparation of strand specific hybridization probes.

This method may be similarly employed to identify cohesive ends present on one or more fragments. Labelling of the fragments with a reporter group such as a 5'-$^{32}$P label followed by ligation to a panel of immobilized indexing linkers results in the reporter group becoming selectively attached to the corresponding complementary indexing linker. The identity of the cohesive ends of the fragment(s) is inferred readily from the identity of the immobilized indexing linker to which the labelled fragment has been attached.

Figure 2:
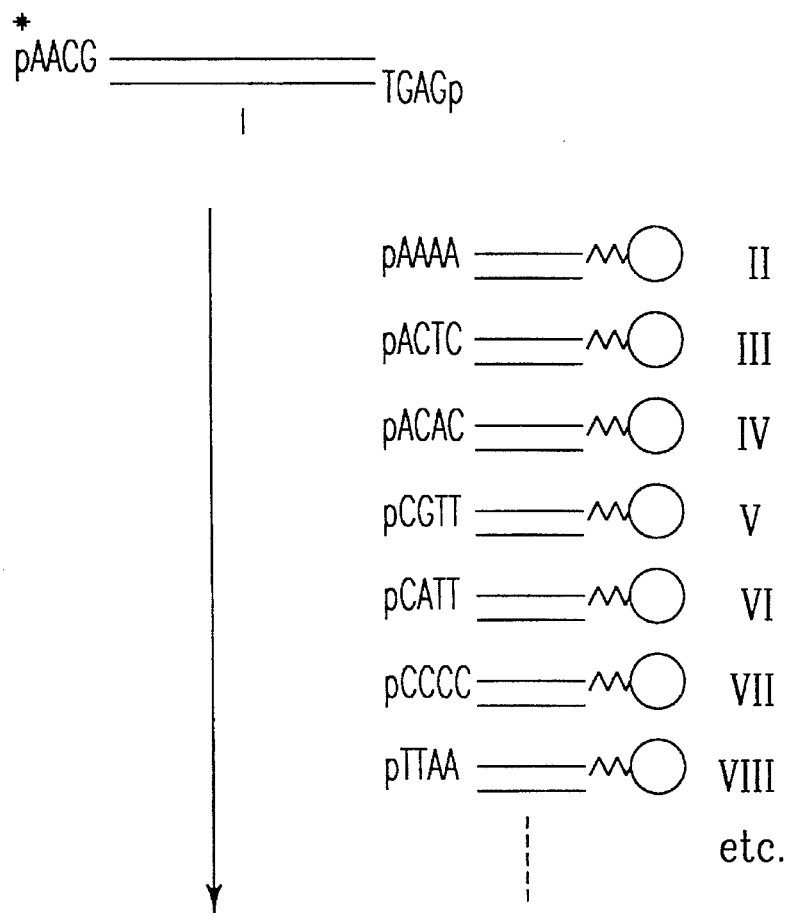
FIG. 2 Schematic diagram showing an example of ligation of DNA to immobilized indexing linkers.
Figure 2:
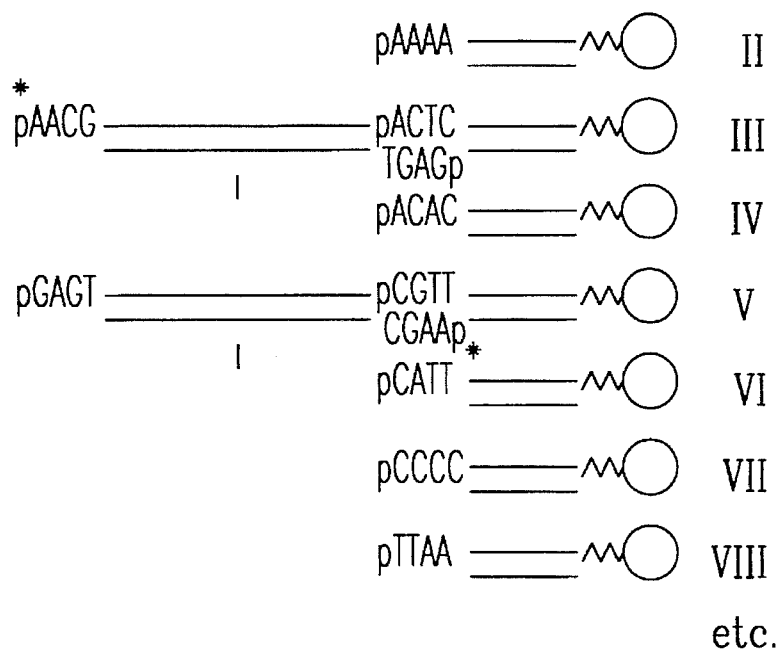

With reference to FIG. 2, ligation of a DNA fragment (I) to a complete panel of indexing linkers (II,III,IV, V, VI, etc) results in selective attachment of I to only those members of the panel having complementary cohesive ends (III,V). If the original DNA fragment I has been labelled with a detectable reporter group (*) then that reporter group will be linked selectively to III and V thus indicating the identity of the cohesive ends of I. Each member of the panel of linkers may be immobilized, as shown in FIG. 2, by covalent attachment of one or both of the strands of the double stranded region of the linker to a suitable substrate. In a preferred embodiment, each member of the panel is attached to spatially separated parts of an insoluble support.

A method for selective amplification of a class of nucleic acid fragments using the polymerase chain reaction requires the attachment of specific indexing linkers to the class of fragments via their complementary cohesive ends. In the presence of complementary primers hybridized to the indexing linker at the 3'-end of each fragment strand, the members of the class, up to the maximum practical size for PCR amplification, may be amplified according to the prior art. Separation of the products on the basis of size permits the isolation of unique fragments. In this way, each amplified fragment of the indexed class can be identified and isolated on the basis of the identity of its cohesive ends and its length.

Complementary primer sequences for hybridization to a linker strand may be prepared according to known procedures, such as the same procedures described herein for preparation of the linker oligonucleotides, and in a preferred embodiment are identical to the strand which provides the 3'-end of the first end of the linker oligonucleotide.

Figure 3A:
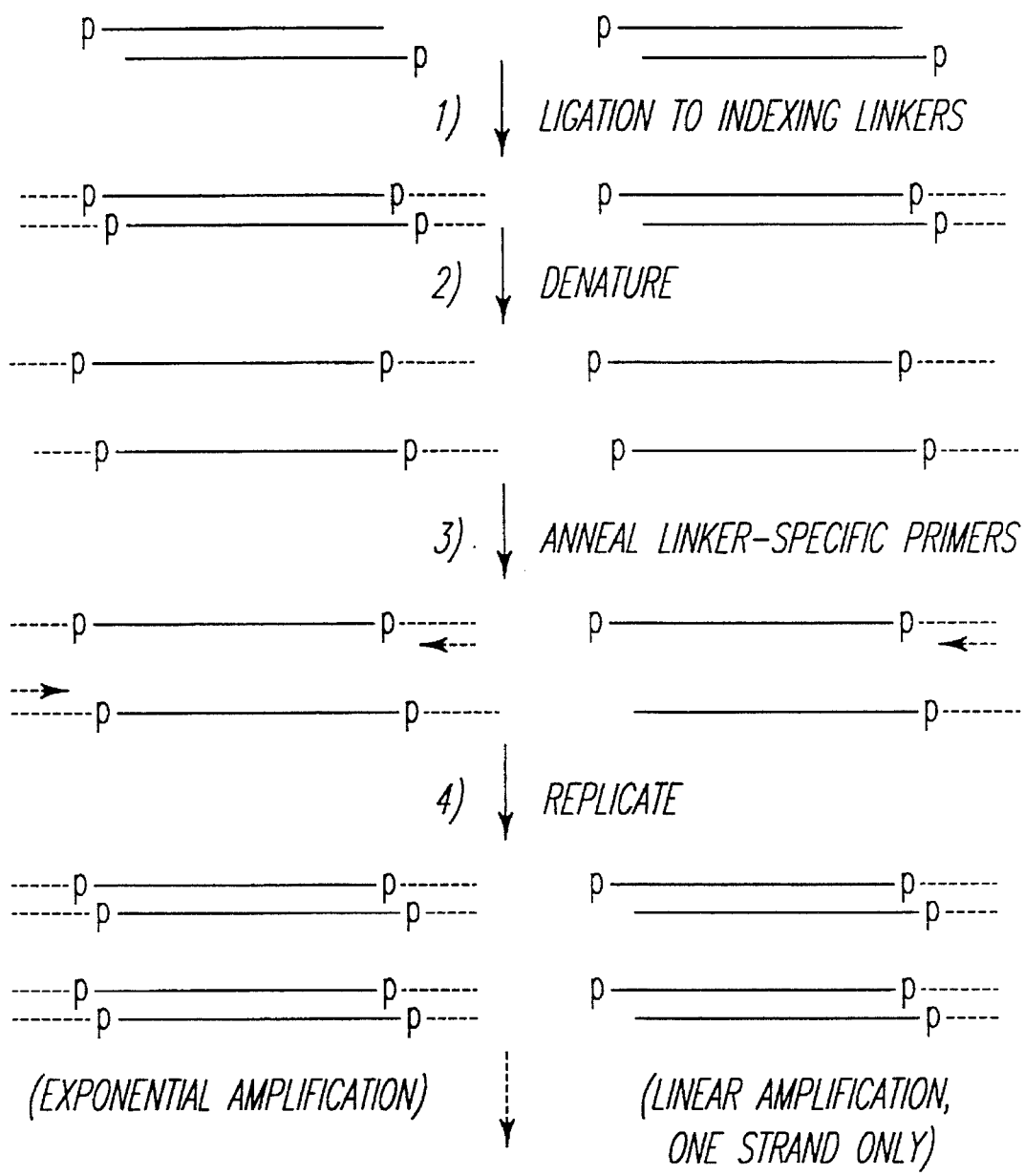
FIG. 3(a) Schematic diagram showing an example of indexed amplification by polymerase chain reaction.

With reference to FIG. 3(a), ligation of one or more indexing linkers (dotted lines) to a mixture of DNA molecules (step 1) gives three types of products: DNA molecules with linkers attached to both ends (shown on the left), DNA molecules with a linker attached to only one end (shown on the right) and DNA molecules with no indexing linkers attached (not shown: these will be inert). Steps 2,3 and 4 constitute the stages of a single cycle of DNA amplification by the polymerase chain reaction. It is understood that the primer strand (indicated by the short arrow) is present in excess. In the third step, the primers will anneal to both strands of the DNA on the left, while on the right, only one strand can be hybridized with primer. Consequently, in the replication (step 4), DNA molecules having indexing linkers at both ends (those having both ends complementary to the indexing linkers used) are fully duplicated, and will be exponentially amplified in subsequent cycles. In contrast, DNA molecules having only one end complementary to the indexing linkers used can have only one strand replicated, resulting in only linear amplification of the one strand.

Thus, in a mixture of DNA fragments having non-identical cohesive ends, attachment of indexing linkers provides known flanking sequences to a selected subset of the DNA fragments and permits selective amplification of that subset. Use of a set of linkers having cohesive ends complimentary to all or some of the variety of possible cohesive ends of fragments in a mixture will permit amplification of fragments whose sequences are unknown.

With the attachment of two indexing linkers, three classes of fragments will be amplified: the class with both ends complementary to the first indexing linker, the class with both ends complementary to the second indexing linker, and finally the class with one of each end. Either of the first two classes can be prevented from being amplified by a variation of this procedure which makes use of a linker which has a 5'-hydroxyl group in place of a 5'-phosphate group at the cohesive end of the indexing linker. The linker strand with the 5'-hydroxyl group will be covalently linked only to the 5'-end of the target fragment's cohesive end, and consequently there would be no primer hybridization site on this strand. During the first round of copying only, the fragments having a covalently attached site for primer hybridization will be copied. When replication reaches the end distal from the primer, then the indexing linker sequence attached to the 5'-end is copied and this provides the necessary new primer hybridization site. Thus, fragments lacking a primer site at both ends cannot be copied (amplified) because neither strand has a primer hybridization site, while molecules with one primer site generate the necessary second primer site in the first round of replication, and are subsequently amplified. Cleavage of the indexing linkers from the two classes of fragments thus amplified followed by ligation to the same pair of indexing linkers where the opposite member of the pair lacks the 5'-phosphate would permit amplification of only the desired class having two different cohesive ends.

Figure 3B:
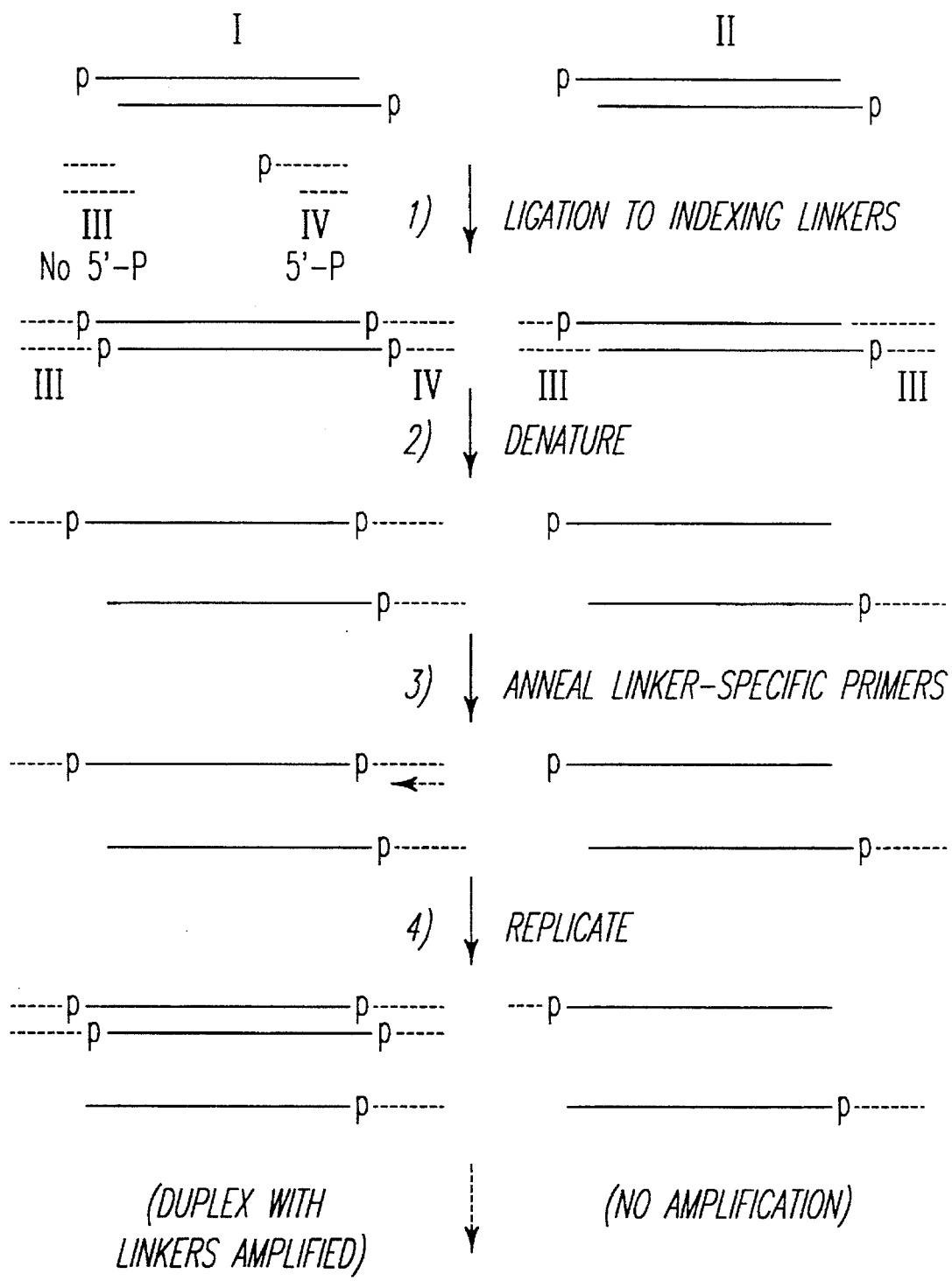
FIG. 3(b) Schematic diagram showing an example of indexed amplification using 5'-P and 5'-OH linkers.

With reference to FIG. 3(b), indexed amplification of DNA fragments containing identical ends can be suppressed by using linkers lacking a 5'-phosphate in the portion of the linker containing the cohesive end. Such a 5'-OH linker will be ligated in only one strand to a 5'-p strand end of a DNA fragment having a corresponding complimentary cohesive end. An example of such a linker is element III of FIG. 3(b) which has a 5'-OH situated at the free end of the single stranded region of the linker. Alternatively, the 5'-OH may be situated at the end of the double stranded region adjacent to the indexing cohesive end in linkers which have a protruding 3'-end.

The 5'-p linker (IV) shown in FIG. 3(b) is joined to both strands. Upon denaturation (step 2) each single strand has a linker sequence at its 5'-end (dotted line). Thus, only one strand of the DNA molecule (I) (which has two different ends) will have a linker sequence attached to its 3'-end, which is required for annealing the primer (short arrow) in step 3. Replication (step 4) is dependent on the presence of the annealed primer. Thus the upper strand of I is the only strand copied (including the linker sequence), resulting in a duplex molecule having linker sequences covalently attached to both ends. In subsequent rounds of amplification, both strands of I (with attached indexing linkers) will be amplified.

In contrast, strands of DNA duplex II shown in FIG. 3(b) will not be replicated at all for lack of a suitable primer site. In this way the amplification of molecules with identical ends can be prevented while amplification of molecules with non-identical ends is readily permitted.

By using indexing linkers, one may not only selectively label a subset of DNA fragments, one may also simultaneously make the label both end and strand specific. Since one strand of the indexing linker also serves as a primer binding site for replication of the target DNA, this technique is expected to be particularly useful for DNA sequencing and for preparing unique strand specific hybridization probes directly from selected DNA fragments. The specificity of the indexing procedure will permit probe synthesis and sequencing in respect of specific fragments of DNA in a mixture (for example, one restriction fragment in a digest of a larger fragment).

A variety of enzymes which act on nucleic acids depend upon certain structural features for their activity. For example the enzyme polynucleotide kinase requires a 5'-hydroxyl terminus as a substrate in order to transfer a phosphate group from ATP to the 5'-end of the DNA. Indexing linkers containing any of a number of structural modifications could be used to introduce the modifications to selected subsets of DNA molecules, thereby permitting the selective application of various enzymatic activities to either the modified or the unmodified subset of DNA molecules. Two such examples are described in FIG. 4.

Figure 4:
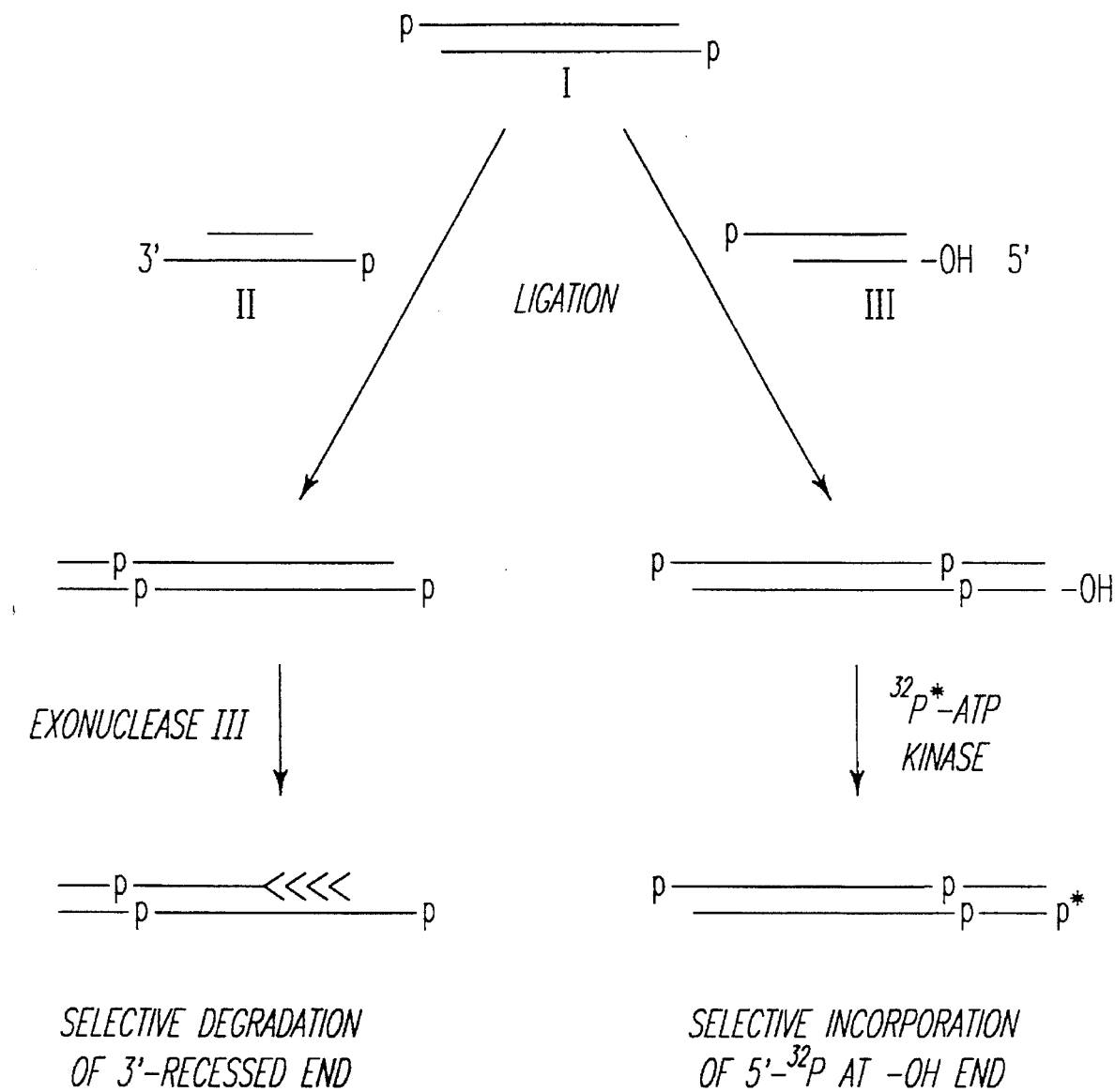
FIG. 4 Schematic diagram showing an example of end specific modification of enzymatic action.

With reference to the right hand side of FIG. 4, the right end of duplex DNA molecule I is modified by selective indexed ligation to a linker (III) with a 5'-OH terminus at the end opposite to the indexing cohesive end. The resulting duplex can be selectively phosphorylated by the enzyme polynucleotide kinase at the attached 5'-OH site.

On the left hand side of FIG. 4, the left end of I is selectively modified by attachment of linker II which has a 3'-protruding end at its non-indexing end (or, second end). Exonuclease III will not digest the left end because of the presence of a 3'-protruding end which is a "non-substrate" for the enzyme. The right end of the molecule is selectively attacked, resulting in the progressive degradation of the upper strand. This would simplify both deletion mapping and DNA "footprinting", procedures which currently require additional manipulation to permit unidirectional exonuclease action or asymmetrical labelling on DNA fragments of interest.

The examples described by reference to FIG. 4 demonstrate the principle that selective incorporation of an indexing linker can enable or disable the action of enzymes which act on nucleic acids depending upon the structure of the linker and the substrate requirements of the enzymes used.

By extension, it is apparent that the actions of polymerases, ligases and other restriction endonucleases may also be directed selectively to one subset of nucleic acid fragments as a result of the incorporation of the appropriate structural features into indexing linkers. For example, the indexing linker may contain a known moiety which blocks the activity of a particular enzyme on the fragment to which the linker is attached. Many manipulations of DNA fragments involved in the construction of particular recombinant DNA molecules involve the use of these enzymes, and the ability to apply their activities selectively is expected to provide significant advantages.

A number of procedures are known in the art which employ the separation of recognition and cleavage sites for Type IIS restriction endonucleases, to permit excision of bases, linker mutagenesis and DNA replacement mutagenesis. These procedures are dependent upon cloning and alone, do not offer the specificity provided by this invention. For example, excision of bases from cloned DNA depends upon the inclusion of a suitably located Type IIS restriction endonuclease recognition sequence adjacent to a DNA insertion site in a cloning vector (see for example: Hasan, N. et al (1986) Gene 50.:55–62, "A Novel Multistep Method for Generating Precise Unidirectional Deletions Using BspMI, a Class-IIS Restriction Enzyme") where the cleavage reaction produces cohesive ends which are subsequently removed in order to permit religation of the resulting blunt ends to form a viable closed double stranded vector DNA molecule). Bidirectional mutations within a DNA sequence have been demonstrated using "excision linkers" containing blunt ends inserted into a suitable site within the DNA sequence (S. Mormeneo et al. (1987) Gene 61:21–30 "Precise nucleotide Sequence Modifications with Bidirectionally Cleaving Class-IIS Excision Linkers" where the cohesive ends produced by cleavage with the appropriate Type IIS enzyme are removed to enable rejoining of the cleaved ends by blunt end ligation).

Insertion or deletion of a few nucleotides into, or from, a nucleic acid fragment can be accomplished by using indexing linkers containing a Type IIS recognition sequence which does not result in cleavage in register with the cohesive end of the indexing linker. Consequently, it is possible to cause cleavage (by the corresponding restriction endonuclease) of fragments to which these indexing linkers have been attached, to reveal a different cohesive end reflecting the addition or deletion of several nucleotides. The present invention permits this process to be applied selectively to either fragment end of a class of fragments with cohesive ends resulting in the production of new ends, conferring additional specificity on the fragments so modified. This additional specificity can be used to distinguish between members of a class of fragments initially containing identical cohesive ends, including those produced by restriction endonucleases recognizing palindromic sequences which produce identical ends at every cleavage site. The process can be applied recursively to generate successive deletions or insertions.

Figure 5:
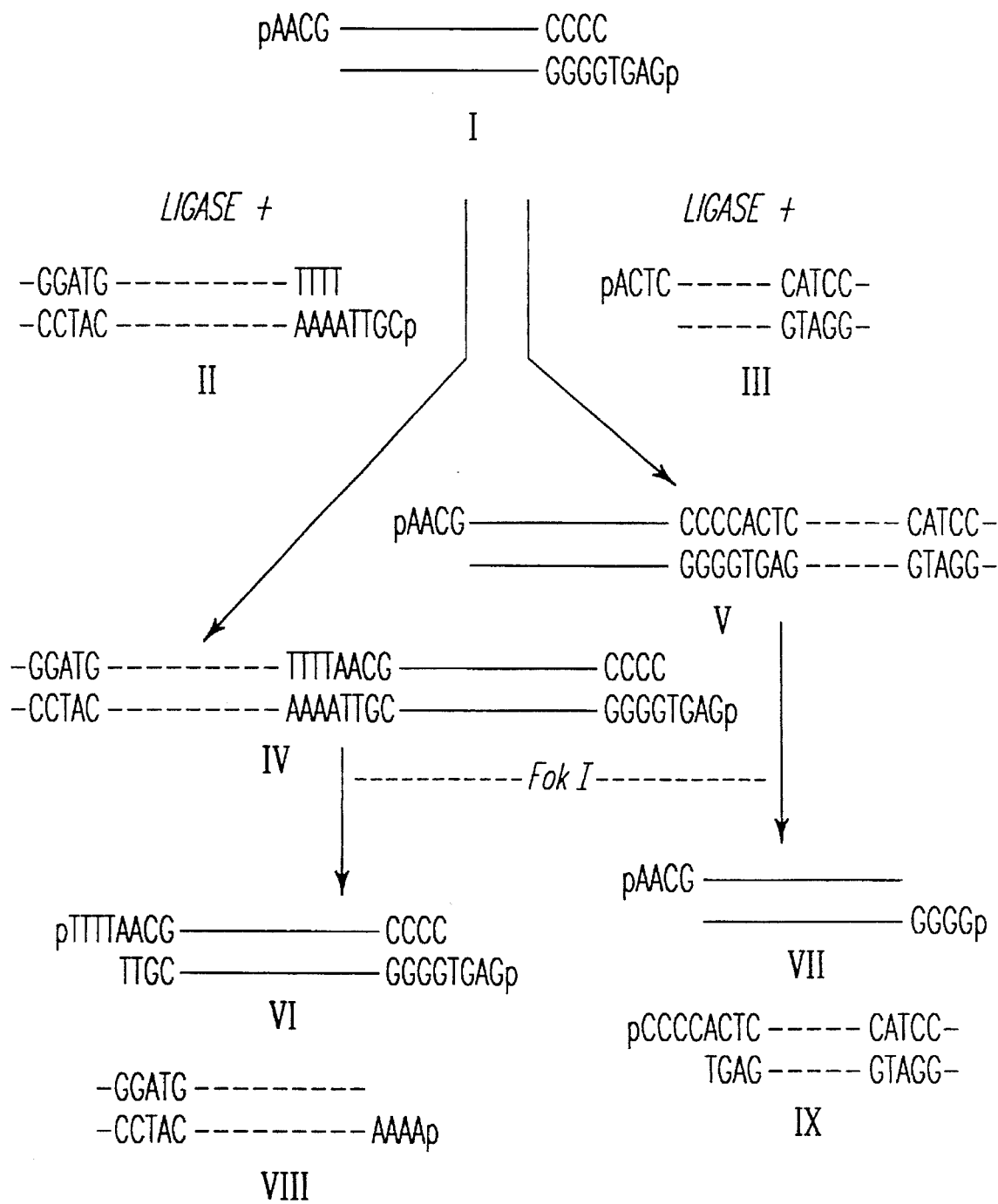
FIG. 5 Schematic diagram showing an example of insertion and deletion using indexing linkers.

An insertion procedure is shown on the left hand side of FIG. 5. Linker (II) is selectively attached to the complementary cohesive end of DNA fragment I. This linker has been constructed with a FokI recognition sequence located 13 bases from the 3' end of the top strand and is oriented so that the cleavage site will be to the left of the TTTT sequence and to the right of the complementary AAAA sequence. Consequently when product IV is cut with FokI, product (VI) corresponds to the attachment of the four base TTTT sequence to I and the filling in of the old cohesive end. The second product (VIII) is a new indexing linker with an AAAA cohesive end.

A deletion procedure is shown on the right side of FIG. 5. Selective attachment of linker III produces V. When V is cut with FokI, the recognition sequence directs cleavage to the left of CCCC in the top strand and to the right of GGGG in the bottom strand. The resulting product VII corresponds to I with its right cohesive end removed and the new GGGG cohesive end revealed. The bases removed have been transferred to the linker giving it a new cohesive end CCCC (IX).

It can be seen that by adjusting the location of the Type IIS recognition sequence that any number of bases may be added to a selected cohesive end and a small number of bases may be deleted. Repeated application of the deletion procedure would permit more bases to be deleted.

The procedures described above offer a variety of ways in which existing methodology can be extended through the application of the current invention. Each one depends upon the selective liganion of one or more of the disclosed indexing linkers to the corresponding complementary cohesive ends of DNA fragments, particularly those released by Type IIS restriction endonucleases.

The invention is described in further detail in the following examples. Examples 1 and 2 represent test systems which were designed using known DNA sequences to study the application of indexing linkers to the identification and amplification of DNA fragments. The plasmid pBR322 contains 12 FokI sites and Bacteriophage Lambda contains 152 FokI sites. From the published sequences, two fragments from each genome were arbitrarily selected as targets. Linkers with four base cohesive ends complementary to the chosen fragment cohesive ends were prepared for use in these procedures.

Example 3 represents an application of indexing linkers to the identification and amplification of unknown fragments in a digest of a large genome. Example 4 demonstrates the specificity of three base, 3'-protruding cohesive end linkers.

In the examples, the linkers were ligated singly or in pairs to the DNA digests and the templates so obtained were subjected to in vitro amplification using a complementary common primer for the polymerase chain reaction technique. It was expected that ligation of the correct linkers to the known target fragments would lead to amplification of the fragment which would be detected directly on agarose gels. For each target DNA, a distinct band of DNA of the correct size should be seen only in the gel lane when the two correct linkers have been used. The appearance of bands of DNA of incorrect size or, the appearance of bands in the absence of either correct linker would indicate misligation of the linkers or some other significant flaw.

All of the linker oligonucleotides described in the examples were synthesized by the phosphoramidite procedure on a Biosearch 8750™ automated synthesizer and were subsequently purified by thin layer chromatography (T. K. Archer et al (1985) J. Biol. Chem. 260:1676–1681 "Apolipoprotein C-II mRNA levels in Primate Liver"). The linkers and primer oligonucleotides synthesized for use in examples 1 and 2 are shown in Table 1. The linkers and primer oligonucleotides synthesized for use in examples 3 and 4 are shown in Table 2. Buffers and reagents used in all examples are described in Table 3 (all components were reagent grade or better).

TABLE I

| Identification No. | Genomic DNA Source | Selected FokI Site | Estimated Average Fragment Length | Fragment Ends | Synthesized Linkers |
|---|---|---|---|---|---|
| 1027 | Lambda | 11,468 | 313 bp | 5'-pATAT- | 5'-pATAT-(common) |
| 1028 | Lambda | 11,189 | 313 bp | 5'-pCGTT- | 5'-pAACG-(common) |
| 1118 | pBR322 | 3,533 | 287 bp | 5'-pCTTT- | 5'-pAAAG-(common) |
| 1119 | pBR322 | 3,820 | 287 bp | 5'-pGAAT- | 5'-pATTC-(common) |

Note:
The common portion of each linker was complementary to oligonucleotide No. 1026, GGATCCGGATGCGAAGACGG, used to form the double stranded part of the linkers.

TABLE II

| Identification No. | Genomic DNA Source | Selected FokI Site | Estimated Average Fragment Length | Fragment Ends | Synthesized Linkers |
|---|---|---|---|---|---|
| 1790 | SV4OL | 5,050 | 192 bp | 5'-pGCAT | 5'-pATGC-common* |
| 1702 | SV4OL | 5,241 | 192 bp | common**AGG3' | common*CCT-3'-common** |
| 1791 | SV4OR | 97 | 102 bp | 5'-pTCCC | 5'-pAGGG-common* |
| 1703 | SV4OR | 5,238 | 102 bp | 3'TCC | 3'GGA-common** |

*the common sequence for these linkers is complementary to oligonucleotide #1504. 5'-GGTACAGGATGCGAAGACAA3', used to form the double stranded part of these linkers.
**the common sequence of these linkers is complementary to oligonucleotide #1701. 5'-pTTAGCGCCTACAACCGGC-3', used to form the complementary part of these linkers.

TABLE III

Buffer A: Ligation Buffer (10×):

0.5M Tris (pH 7.4) (TRIZMA; SIGMA*)
0.1M MgCl2
1.1M dithiothreitol (SIGMA*)
10 mM spermidine (SIGMA*)
10 mM ATP (SIGMA*)
1 mg/mL BSA (Calbiochem*)

Buffer B: Endonuclease Digestion Buffer (10×):

1.5M NaCl
0.1M Tris (pH 7.5)
0.1M MgCl2
10 mM dithiothreitol (SIGMA*)

Buffer C: PCR Buffer (10×):

0.1M Tris, (pH 8.3)
0.5M KCl
25 mM MgCl2
0.1% Gelatin dNTP MIXTURE (SIGMA*):

10 mM dATP
10 mM dGTP
10 mM dCTP
10 mM dTTP

Buffer D: Resuspension Buffer:

10 mM Tris (pH 7.6)
1 mM CDTA (pH 8.0) (SIGMA*)

ENZYMES:

T4 DNA Ligase (US Biochemical*)
TaqI DNA Polymerase (Bethesda Research Laboratories (BRL)*)
FokI; HpaII; PstI; SfiI (New England Biolabs*)

DNA:

pBR322 (Pharmacia*)
Lambda phage (New England Biolabs*)
SV40 (BRL)
E. Coli (Calbiochem*)

*Trade mark/trade name

EXAMPLE I

INDEXING-LINKER-SPECIFIC AMPLIFICATION OF PARTICULAR DNA FRAGMENTS USING FOUR BASE 5'-PO4 INDEXING LINKERS; FokI indexing linker amplification of defined fragment from pBR322.

DNA: 10 μg of closed covalent circular pBR322 DNA was digested in Buffer B for four hours with 20 U of FokI restriction endonuclease, ethanol precipitated and resuspended in Buffer D at 50 ng/μl. The methods used to cut pBR322 using FokI are described on pages 98 to 106 of Maniatis et al, *Molecular Cloning—A Laboratory Manual* [supra]. All methods, unless specified are described in Maniatis, et al; *Molecular Cloning—A Laboratory Manual* [supra].

Indexing Linkers: 4-base 5'-PO$_4$ indexing linkers #1027 (ATAT), #1028 (AACG), #1118 (AAAG) and #1119 (CTTA) were suspended in sterile distilled water (SDW) at 20 pM/µL together with an equal concentration of common primer (oligonucleotide #1026; Table I) and diluted to 20 fM/µl for ligation to digested pBR322 DNA. Ligation conditions were as follows: samples containing 250 ng of DNA (5 µl), 2 µl Buffer A, linker/primer suspension, and SDW to 19 µl were heated to 60° C. for $2^{min}$; cooled to 37° C., 1.3 U ligase (1 µl) added followed by $15^{min}$ incubation, and heating to 95° C. for $1^{min} 30^{sec}$ to inactivate ligase and denature DNA. DNA was precipitated 30' at −20° C. spun out $5^{min}$ at room temperature and resuspended in 20 µl of Buffer D.

Ligations of pBR322: four samples were prepared according to the following scheme:

| SAMPLE REFERENCE | LINKER | VOLUME OF LINKER/PRIMER SUSPENSION (20 fM/µl) |
|---|---|---|
| A | 1118 | 1 µl |
| B | 1119 | 1 µl |
| C | 1118/1119 | 2 µl |
| D | 1027/1028 | 2 µl |

PCR Amplification of pBR322 Fragments (following procedure described in "PCR—Technology—Principles and Applications for DNA Amplification"; H. A. Erlich (Ed.); Stockton Press; New York, pages 13–20): 2.5 µl of the ligated DNA samples were mixed with 5 µl of Buffer C, 8 µl of dNTP's, 33.25 µl SDW, 0.25 µl (1 U) of Tag I DNA polyerase and 1 µl (20 pM) primer (#1026), and amplified in accordance with the following cycle: #1:72° C.,$2^{min}$; #2:95° C.,$1^{min}30^{sec}$; #3:55° C.,$2^{min}$; #4:72° C.,$5^{min}$; #5: cycle to #2 29 times; #6:72° C.,$5_{min}$; #7 end. Analysis was performed on 1.8% agarose gels in TPE.

Results: The gel is shown in FIG. 6. Lane 1 shows molecular weight markers. Lane #2 (sample A) shows no amplification of the target fragment between base pairs 3,515 and 3,806 using only linker #1118 from Table 1. Lane #3 (sample B) shows the absence of amplification product when only linker #1119 from Table 1 is used. Lane #4 (sample C) shows that the linkers #1118 and #1119 from Table 1 lead to the amplification of a fragment consistent with the piece between base pairs 3,515 and 3,806 of pBR322 and including two 20 bp indexing linkers. Lane #5 shows the digestion of the amplified fragment of sample C, by the restriction endonuclease PstI, resulting in two fragments, with molecular sizes indicating than the PstI site was as expected from amplification of the pBR322 fragment between bp 3515 and 3806. Lane 6 (sample D) shows use of the heterologous linkers #1027 and #1028 in ligation with no detectable amplification product. Accordingly, the target DNA was indexed and amplified as expected by indexing linkers 1118 and 1119 and primer 1026.

EXAMPLE 2

This example is similar to Example 1, but the more complex genome of Lambda phage was employed.

DNA: 10 µg of phage Lambda DNA was digested 4 hours at 37° C. with 20 U of FokI restriction endonuclease in Buffer B and ethanol precipitated for resuspension in Buffer D.

Indexing Linkers: 4-base 5'-PO$_4$ indexing linkers #1027 (ATAT), #1028 (AACG), #1118 (AAAG) and #1119 (CTTA) were suspended in SDW at 20 pM/µL together with an equal concentration of common primer #1026 and diluted 1000 fold in SDW for ligation to digested phage Lambda DNA. Ligation conditions as follows: samples containing 250 ng DNA (5 µl), 2 µl Buffer A, linker/primer suspension, and SDW to 19 µl were heated to 60° C. for $2^{min}$ and cooled to 37° C.; 1.3 U (1 µl) ligase added with $15^{min}$ incubation; heating to 95° C. for $1^{min}30^{sec}$ to inactivate ligase and denature DNA. DNA was precipitated $30^{min}$ at −20° C. spun out $5^{min}$ at room temperature and resuspended in 20 µL Buffer D.

Ligations of phage Lambda: four samples were prepared according to the following scheme:

| SAMPLE | LINKER | VOLUME OF LINKER/PRIMER SUSPENSION (20 fM/µl) |
|---|---|---|
| A | 1027 | 1 µl |
| B | 1028 | 1 µl |
| C | 1027/1028 | 2 µl |
| D | 1118/1119 | 2 µl |

PCR Amplification of phage Lambda Fragments (following procedure of example 1): 2.5 µl samples of the ligated DNA were mixed with 5 µl Buffer C, 8 µl of NTP's, 33.25 µl water, 1 U TaqI DNA polymerase in 0.25 µl and 20 pM primer (#1026) in 1 µl, and amplified in accordance with the following cycle. #1.72° C. $2^{min}$; #2:95° C.,$1_{min}30^{sec}$; #3:55° C.,$2^{min}$; #4:72° C.,$5^{min}$; #5: cycle to #2, 29 times; #6:72° C.,$5^{min}$; #7 end. Gel analysis was carried out as described in Example 1 and is shown in FIG. 7.

Results: In Lane #1, the molecular weight marker serves to standardize the gel. In Lanes 2 (sample A) and 3 (sample B), use of indexing linkers #1027 and #1028 from Table 1 lead to no detectable product. In Lane #4, the presence of linkers #1027 and #1028 (sample C) during ligation lead to the amplification of a fragment of DNA with the molecular weight expected of the FokI fragment between 11172 and 11485, with addition of two 20 bp indexing linkers to the fragment. In Lane #5 digestion of the sample C product with the restriction endonuclease HpaII leads to the generation of a fragment about 166 bp long, another about 131 bp long, and shorter pieces of 30 bp or less, as expected from digestion of a fragment generated between the FokI sites tested. No fragments were generated in sample D when indexing linkers #1118 and #1119 were used in ligation, as shown in Lane #6.

EXAMPLE 3

OBSERVATION OF AMPLIFICATION OF PARTICULAR DNA MOLECULES FROM COMPLEX MIXTURES OF FRAGMENTS OF THE DNA OF *E. COLI*:

DNA DIGESTION: 10 µg of *E. coli* DNA was digested for 16 hours with 20 U FokI endonuclease in Buffer B at 37° C. and ethanol precipitated prior to suspension in Buffer D at 50 ng/µL.

LIGATION: 250 ng (5 µl) samples of DNA were ligated to no linkers, not ligated, or ligated in all single and pair-wise combinations to the panel of linkers listed in Table 1 following the procedure of Example 2. It is expected that the approximately $4.7 \times 10^6$ base pairs present in *E. coli* would be cleaved by FokI into about 9000 fragments, which might have any combination of cohesive ends, including by chance those complementary to the panel in Table 1. Furthermore, by chance alone, it would be expected that the probability of generating fragments having two ends identical to each other and to a linker from the panel would be about 9000/32896 or approximately 0.25. Four linkers produce ten combinations of single or paired linkers. If any fragments are present with homologous or heterologous pairs of ends complementary to any one, or any pair of linkers from the panel, such fragments will be ligated to the linkers and will become targets for amplification.

Ligations: 11 samples were prepared according to the following scheme (the primer is oligonucleotide #1026; sample B had no ligase added):

| SAMPLE | DNA | LINKER | VOLUME OF LINKER/PRIMER SUSPENSION (20 fM/µl) |
|---|---|---|---|
| A | None | None | None |
| B | 250 ng | None | None |
| C | 250 ng | None | None |
| D | 250 ng | 1027 | 1 µl |
| E | 250 ng | 1028 | 1 µl |
| F | 250 ng | 1118 | 1 µl |
| G | 250 ng | 1119 | 1 µl |
| H | 250 ng | 1027/1028 | 2 µl |
| I | 250 ng | 1027/1118 | 2 µl |
| J | 250 ng | 1027/1119 | 2 µl |
| K | 250 ng | 1028/1118 | 2 µl |
| L | 250 ng | 1028/1119 | 2 µl |
| M | 250 ng | 1118/1119 | 2 µl |

Figure 8:
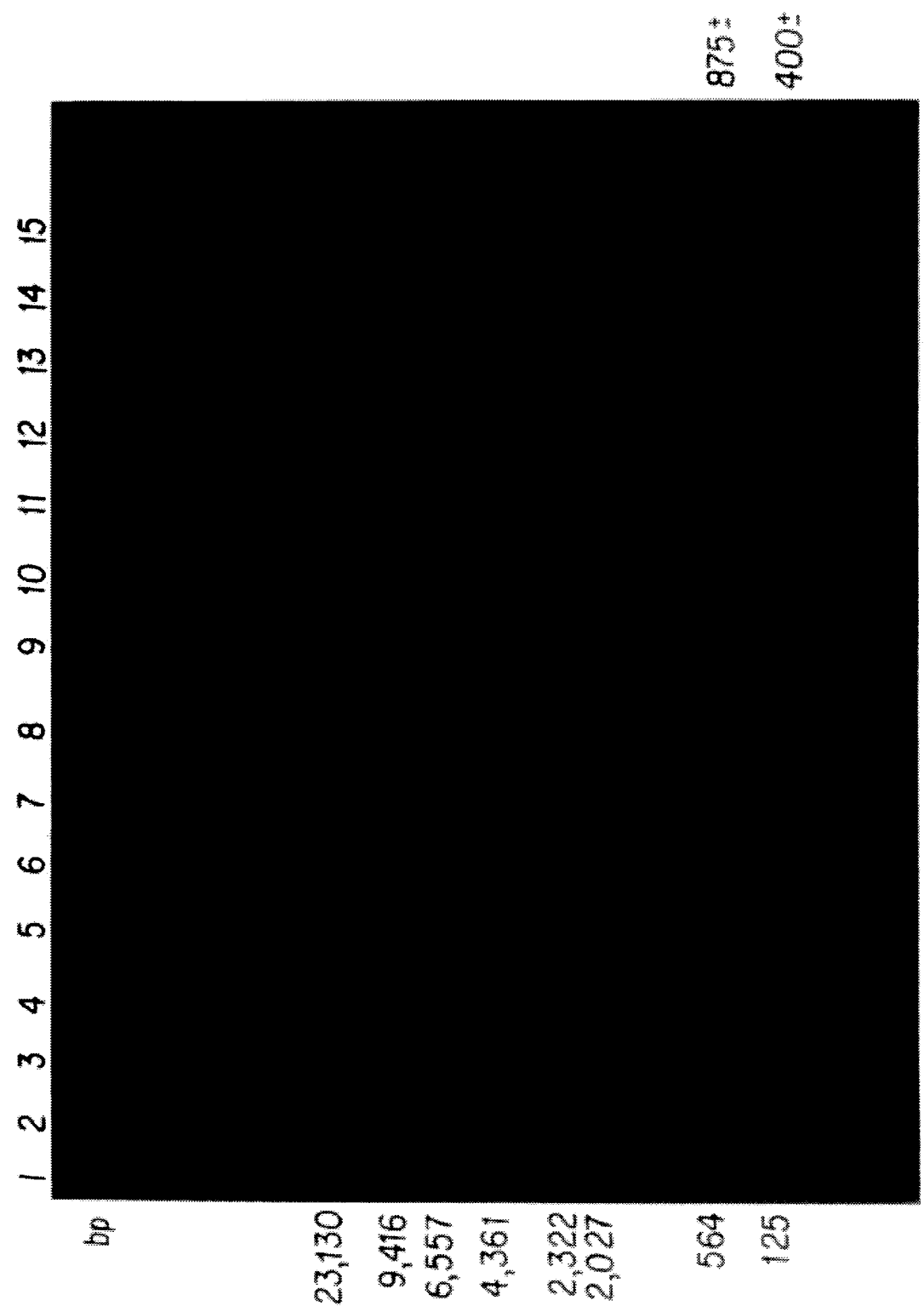
FIG. 8 Photograph of electrophoresis gel described in example 3.

PCR amplification: ligated DNA samples were suspended in Buffer C and the procedure of the preceding examples used. Analysis was performed in 0.8% agarose gels, shown in FIG. 8.

RESULTS: Lane 1 (sample A) shows that primers alone do not lead to products in the PCR reaction. Lane 2 (sample B) shows no product when unligated DNA is incubated with primers. Lane 3 (sample C) shows that DNA ligated in the absence of indexing linkers does not amplify components in reaction mixtures containing primers. Lanes 4 and 12 are molecular weight markers consisting of HinDIII digested phage Lambda DNA. Lane 5 (sample D) shows no bands when linker #1027 is ligated to the mixture by itself. Lane 6 (sample E) shows the amplification of a band of DNA of about 400 base pairs when linker #1028 is ligated. Lane 7 (sample F) shows the amplification of a single fragment of molecular weight about 875 base pairs with linker 1118. Lane 8 (sample 6) shows no product for linker #1119. To test the possibility that fragments with non-identical ends might be present in the reaction mixtures, pair-wise combinations were analyzed. Neither #1027 nor #1119 form amplifiable combinations alone (Lanes 5 and 8), or in combination as shown in Lane 11 (sample J). Furthermore, lane 9 (sample H) only shows the 400 base pair band expected for mixtures containing #1028, and Lane 10 (sample I) only shows the 875 base pair fragment expected for #1118. Lane 13 (sample K) shows the two bands expected if the 400 and 875 base pair fragments are ligated and amplified independent of each other, and this conclusion is proven in Lanes 14 (sample L) and 15 (sample M) where the 400 and 875 base pair bands are observed in the expected reaction mixtures. These figures show that a complex mixture of digestion fragments can be consistently and reproducibly indexed using indexing linkers to lead to the amplification of fragments defined by the complementary sequences of the ends revealed by enzyme digestion. The production of a pair of fragments independently as predicted on the basis of their individual cohesive ends (Lane 13) indicates that indexing of multiple fragments in complex mixtures will occur.

EXAMPLE 4

LIGATION OF 3 BASE, 3'-OH INDEXING LINKERS AND 4 BASE 5'-PO$_4$ LINKERS TO SPECIFIC ENDS IN A MIXTURE AND SPECIFIC AMPLIFICATION OF THE PRODUCTS:

SV40 DNA Digestions: 10 µg of closed covalent circular SV40 DNA was suspended in 200 µL Buffer B and digested with 50 Units of SfiI endonuclease at 50° C. for 16 hours. The DNA was further digested for 4 hours with 20 Units of FokI endonuclease, precipitated in ethanol, and stored in Buffer D. One SfiI cleavage and eleven FokI cleavage sites are expected, with the SfiI cleavage site at base pairs 5238/5241 between FokI sites cleaving at 5050 and 97 base pairs on the standard map. These cleavages produce two fragments having a 5'-four base overhanging cohesive end and a 3'-three base overhanging end, of about 191 and 102 base pairs length. Proof of specific ligation consists of amplifying molecules of a total length of about 231 and 142 base pairs if the relevant indexing linkers have been specifically ligated to the designated target molecules, and have provided binding sites for the relevant synthesis primers.

Ligations: The linkers and complementary primers are shown in Table 2 with the indexing sequences to which the linkers are complementary. The SfiI indexing linkers comprise a complementary common sequence (CS) 5'-pCGGCCAACATCCGCGAAT which ligates to the 3'-strand end of the fragment, and an indexing sequence which serves to both index the cohesive end revealed on endonuclease digestion and act as the primer in subsequent amplification reactions (the same is true for any indexing linker with a 3'-overhang). Ligations were performed using self annealed FokI double stranded indexing linkers, and self annealed double stranded SfiI linker-primer indexing linkers, according to the procedure described for example 2. The following ligation samples were prepared:

| SAMPLE | LINKER AND PRIMER | (VOL. USED 20 fM/µl) | LINKER-PRIMER | (VOL. USED 20 fM/µl) |
|---|---|---|---|---|
| X | 1790/1504 | (1) | 1702 | (1) |
| Y | 1791/1504 | (1) | 1703 | (1) |

PCR: was performed on ligated samples X and Y according to the procedure of the preceding examples under the folliowing scheme:

| SAMPLE | LIGATION SAMPLE USED | EXCESS PCR PRIMERS ADDED |
|--------|----------------------|--------------------------|
| A | X | 1504/1702 |
| B | X | 1504/1703 |
| C | Y | 1504/1703 |
| D | Y | 1504/1702 |

Figure 9:
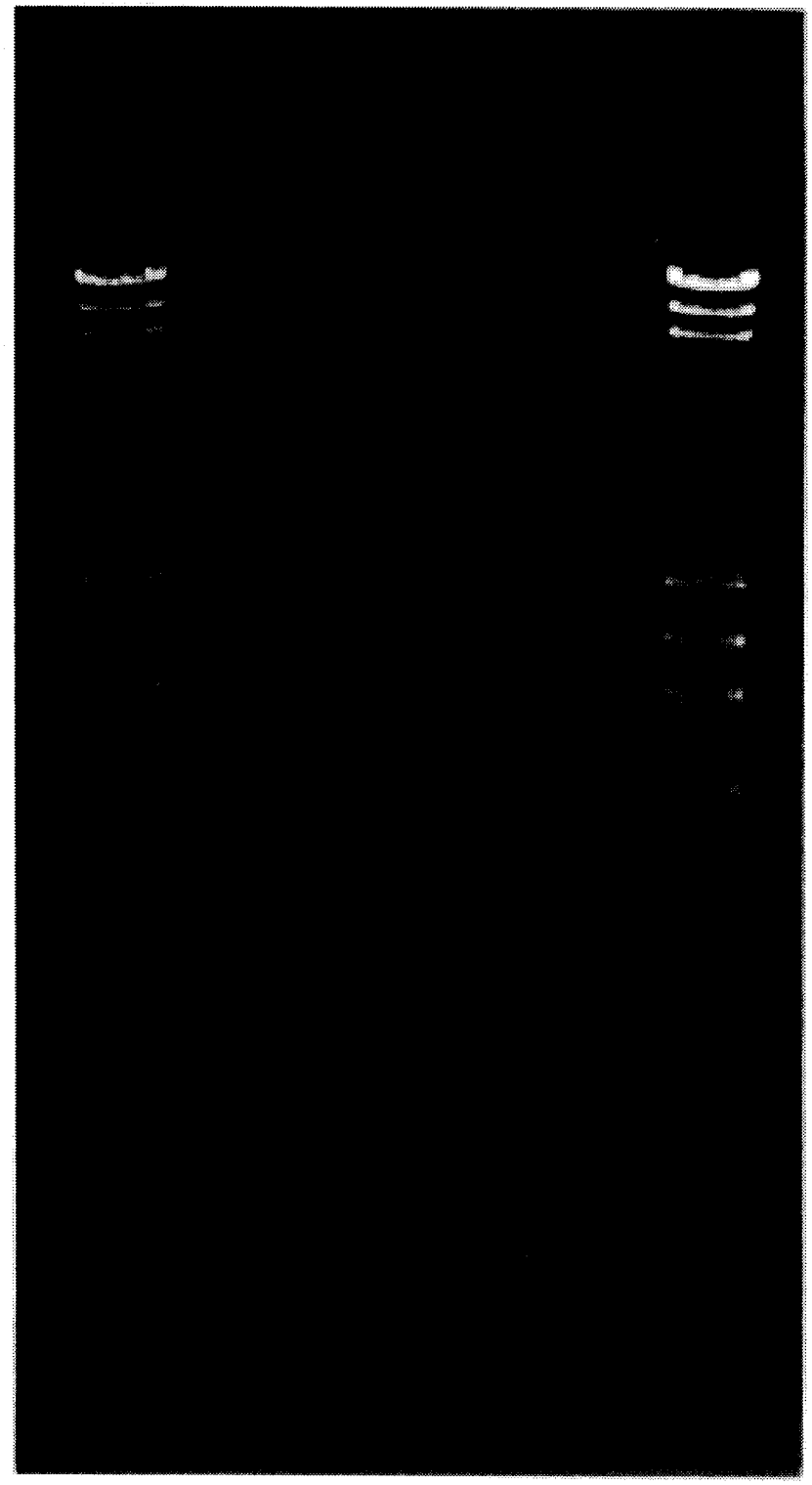
FIG. 9 Photograph of electrophoresis gel described in example 4.

Analysis was carried out according to the procedure of example 3. FIG. 9 shows the resulting gel.

Results: Lane 1 shows molecular weight standards. Lane 2 (sample A) shows amplification of a DNA molecule of c.a. 240 base pairs relative mobility. Lane 3 (sample B) shows that the presence of the incorrect indexing-linker/primer #1703, not present in the original ligation mix, does not lead to the replication of the target molecule. Lane 4 (sample C) shows the amplification of a DNA molecule of about 140 base pairs. Specificity of amplification is shown in Lane 5 (sample D) in which the presence of the incorrect indexing-linker/primer #1702 does not lead to the replication of the target molecule. Lane 6 shows molecular weight standards. Accordingly, indexing linkers with 5'- or 3'-, 3 or 4 base overhangs may be used to selectively index DNA fragments.

As will be obvious to one skilled in the art, many modifications on the invention are possible without departing from the spirit and scope thereof.

We claim:

1. A method for obtaining indexed DNA fragments from a mixture of DNA fragments, for identifying, isolating, mapping, amplifying, or sequencing said fragments, said method comprising:

(i) treating DNA with a restriction endonuclease which is selected from the group consisting of Type IIS restriction endonucleases and restriction endonucleases which recognize interrupted palindromic sequences, to produce DNA fragments having at least one 3'- or 5'-protruding single strand;

(ii) adding said DNA fragments to a set of indexing linkers; each said indexing linker being a DNA duplex having one 3'- or 5'-protruding single strand of a length corresponding to the length of the 3'- or 5'-protruding single strand of the cleavage site of said restriction endonuclease, wherein said set comprises a collection of said indexing linkers whose 3'- or 5'-protruding single strands collectively encode up to all possible permutations and combinations of nucleotides, A, C, G and T, and wherein each indexing linker in said set is physically separated from every other indexing linker in said set;

(iii) contacting said DNA fragments added to said set of indexing linkers with a DNA ligase to cause a selective ligation of those indexing linkers whose 3'- or 5'-protruding single strands are fully complementary to the 3'- or 5'-protruding single strands of the DNA fragments; and (iv) obtaining indexed DNA fragments.

2. The method of claim 1, wherein said process further comprises a step (v) of identifying an indexed DNA fragment.

3. The method of claim 1, wherein said process further comprises a step (v) of isolating an indexed DNA fragment.

4. The method of claim 1, wherein said process further comprises a step (v) of mapping an indexed DNA fragment.

5. The method of claim 1, wherein said process further comprises a step of (v) subjecting an indexed DNA fragment to an amplification reaction to obtain the selective amplification of said DNA fragment.

6. The method of claim 5, wherein said amplification is preformed by cloning.

7. The method of claim 5, wherein said amplification is preformed by the polymerase chain reaction.

8. The method of claim 5, wherein said process further comprises a step (vi) of sequencing said amplified DNA fragment.

9. The method of claim 1, wherein said indexing linkers are immobilized.

10. The method of claim 1, wherein said indexing linkers are covalently labelled with a fluorescent tag.

11. The method of claim 1, wherein said indexing linkers are covalently labelled with a radioisotope label.

12. The method of claim 1, wherein said indexing linkers are covalently labelled with an affinity ligand.

13. A method for obtaining indexed DNA fragments from a mixture of DNA fragments, for identifying, isolating, mapping, amplifying, or sequencing said fragments, said method comprising:

(i) treating DNA with a restriction endonuclease which is a member selected from the group consisting of Type IIS restriction endonucleases and restriction endonucleases which recognize interrupted palindromic sequences, to produce DNA fragments having at least one 3'- or 5'-protruding single strand;

(ii) adding said DNA fragments to two sets of indexing linkers, wherein;

each member of a set of indexing linkers is a common DNA duplex having one 3'- or 5'-protruding single strand of a length corresponding to the length of the 3'- or 5'-protruding single strand of the cleavage site of said restriction endonuclease, said 3'- or 5'-protruding single strand of the member of a set encoding collectively up to all permutations and combinations of nucleotides, A, C, G and T; said members of a set being physically separated from each other;

wherein the common DNA duplex of each of said two sets of indexing linkers is different; and wherein at least one indexing linker from one set of indexing linkers is physically present with at least one indexing linker from the other set of indexing linkers;

(iii) contacting said DNA fragments added to said two sets of indexing linkers with a DNA ligase to cause a selective ligation of those indexing linkers whose 3'- or 5'-protruding single strands are fully complementary to the 3'or 5'-protruding single strands of the DNA fragments; and (iv) obtaining indexed DNA fragments.

14. The method of claim 13, wherein said process further comprises a step of (v) of identifying an indexed DNA fragment.

15. The method of claim 13, wherein said process further comprises a step (v) of isolating an indexed DNA fragment.

16. The method of claim 13, wherein said process further comprises a step (v) of mapping an indexed DNA fragment.

17. The method of claim 13, wherein said process further comprises a step of (v) subjecting an indexed DNA fragment to an amplification reaction to obtain the selective amplification of said DNA fragment.

18. The method of claim 17, wherein said amplification is preformed by cloning.

19. The method of claim 17, wherein said amplification is preformed by the polymerase chain reaction.

20. The method of claims 17, wherein said process further comprises a step (vi) of sequencing said amplified DNA fragment.

21. The method of claim 13, wherein said indexing linkers are immobilized.

22. The method of claim 13, wherein said indexing linkers are covalently labelled with a fluorescent tag.

23. The method of claim 13, wherein said indexing linkers are covalently labelled with a radioisotope label.

24. The method of claim 13, wherein said indexing linkers are covalently labelled with an affinity ligand.

25. A kit for obtaining indexed DNA fragments from a mixture of DNA fragments, for identifying, isolating, mapping, amplifying, or sequencing said fragments, said kit comprising two sets of indexing linkers, wherein:
  (i) each member of a set of indexing linkers is a common DNA duplex having one 3'- or 5'-protruding single strand of a length corresponding to the length of a 3'- or 5'-protruding single strand of the cleavage site of a Type IIS restriction endonuclease or restriction endonuclease recognizing interrupted palindromic sequences;
  (ii) said 3'- or 5'-protruding single strands of the members of at least one set encode collectively at least eight different permutations and combinations of the nucleotides, A, C, G and T;
  (iii) said members of a set being physically separated from each other on the basis of the identity of their 3'- or 5'-protruding end;
  (iv) said two sets of indexing linkers being distinguished from each other on the basis of the identity of their DNA duplexes; and
  (v) said indexing linkers being arranged in pairwise combinations on the basis of the identity of their DNA duplexes.

26. The kit according to claim 25, wherein said indexing linkers are immobilized.

27. The kit according to claim 25, wherein said indexing linkers are covalently labelled with a fluorescent tag.

28. The kit according to claim 25, wherein said indexing linkers are covalently labelled with a radioisotope label.

29. The kit according to claim 25, wherein said indexing linkers are covalently labelled with an affinity ligand.

30. A method for obtaining indexed DNA fragments from a mixture of DNA fragments, for identifying, isolating, mapping, amplifying, or sequencing said fragments, said method comprising:
  (i) treating DNA with a restriction endonuclease which is a member selected from the group consisting of Type IIS restriction endonucleases and restriction endonucleases which recognize interrupted palindromic sequences, to produce DNA fragments having at least one 3'- or 5'-protruding single strand;
  (ii) combining said DNA fragments with a set of indexing linkers and DNA ligase;
    wherein each said indexing linker being a DNA duplex having one 3'- or 5'-protruding single strand of a length corresponding to the length of the 3'- or 5'-protruding single strand of the cleavage site of said restriction endonuclease, wherein said set comprises a collection of said indexing linkers whose 3'- or 5'-protruding single strands collectively encode up to all possible permutations and combinations of nucleotides, A, C, G and T, and wherein said indexing linkers are physically separated from each other;
  such that indexing linkers whose 3'- or 5'-protruding single strands are fully complementary to said 3'- or 5'-protruding single strands of each DNA fragments are ligated; and
  (iii) obtaining indexed DNA fragments.

31. A method for obtaining indexed DNA fragments from a mixture of DNA fragments, for identifying, isolating, mapping, amplifying, or sequencing said fragments, said method comprising:
  (i) treating DNA with a restriction endonuclease which is a member selected from the group consisting of Type IIS restriction endonucleases and restriction endonucleases which recognize interrupted palindromic sequences, to produce DNA fragments having at least one 3'- or 5'-protruding single strand;
  (ii) combining said DNA fragment with a set of indexing linkers and DNA ligase;
    wherein each said indexing linker being a DNA duplex having one 3'- or 5'-protruding single strand of a length corresponding to the length of the 3'- or 5'-protruding single strand of the cleavage site of said restriction endonuclease, wherein said set comprises a collection of said indexing linkers whose 3'- or 5'-protruding single strands collectively encode up to all possible permutations and combinations of nucleotides, A, C, G and T, and wherein said indexing linkers are physically separated from each other;
  such that indexing linkers whose 3'- or 5'-protruding single strands are fully complementary to said 3'- or 5'-protruding single strands of each DNA fragments are ligated to form a mixture of indexed dsDNA fragments; and
  (iii) amplifying at least one of said indexed DNA fragments.

32. The method of claim 31, wherein said amplification step (iii) comprises:
  (a) denaturing said indexed dsDNA fragments to obtain indexed ssDNA fragments;
  (b) contacting said mixture of indexed ssDNA fragments with two oligonucleotide primers which are fully complementary to each indexing linker ligated at the 3'- and 5'-ends of said indexed ssDNA fragment,
  (c) treating the reaction mixture of step (b) with DNA polymerase to obtain a new dsDNA molecule which is identical to said indexed dsDNA fragment obtained in step (ii),
  (d) denaturing the dsDNA obtain in step (c) and repeating steps (a)–(c).

33. In a polymerase chain reaction kit comprising: heat source, oligonucleotide primers, DNA polymerase and a mixture of all four deoxynucleotide precursors, wherein the improvement comprises:
  a panel for obtaining indexed DNA fragments from a mixture of DNA fragments, for identifying, isolating, mapping, amplifying, or sequencing said fragments,
  said panel comprising a set of indexing linkers, each said indexing linker being a DNA duplex having one 3'- or 5'-protruding single strand of a length corresponding to the 3'- or 5'-protruding single strand of the cleavage site of a Type IIS restriction endonuclease or a restriction endonuclease recognizing interrupted palindromic sequences, wherein said set comprises a collection of indexing linkers whose 3'- or 5'-protruding single strands collectively encode up to all possible permutations and combinations of the nucleotides, A, C, G and T, and wherein said indexing linkers are physically separated from each other on the basis of the identity of their 3'- or 5'-protruding single strand.

* * * * *